US00PP24812P2

(12) United States Plant Patent
Zureick

(10) Patent No.: US PP24,812 P2
(45) Date of Patent: Aug. 26, 2014

(54) ***CORNUS* PLANT NAMED 'NEIL Z'**

(50) Latin Name: *Cornus sericea*
Varietal Denomination: Neil Z

(71) Applicant: Neil Zureick, Cincinnati, OH (US)

(72) Inventor: Neil Zureick, Cincinnati, OH (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 44 days.

(21) Appl. No.: 13/694,553

(22) Filed: Dec. 12, 2012

(51) Int. Cl.
*A01H 5/00* (2006.01)

(52) U.S. Cl.
USPC ..... Plt./220

(58) Field of Classification Search
CPC ..... A01H 5/00; A01H 5/02
USPC ..... Plt./220
See application file for complete search history.

*Primary Examiner* — Kent L Bell
(74) *Attorney, Agent, or Firm* — C. A. Whealy

(57) ABSTRACT

A new and distinct cultivar of *Cornus* plant named 'Neil Z', characterized by its upright and compact plant habit; moderately vigorous growth habit; and thick, glossy, relatively small and rugose leaves.

2 Drawing Sheets

Botanical designation: *Cornus sericea.*
Cultivar denomination: 'NEIL Z'.

BACKGROUND OF THE INVENTION

The present invention relates to a new and distinct cultivar of *Cornus* plant, commercially produced as an ornamental shrub, botanically known as *Cornus sericea* and hereinafter referred to by the name 'Neil Z'.

The new *Cornus* plant is a naturally-occurring branch mutation of an unnamed selection of *Cornus sericea* (also known as *Cornus stolonifera*), not patented. The new *Cornus* plant was discovered and selected by the Inventor from within a population of plants of the unnamed selection in a controlled outdoor nursery environment in Cincinnati, Ohio in June, 2003.

Asexual reproduction of the new *Cornus* plant by softwood cuttings in a controlled environment in Cincinnati, Ohio since June, 2008 has shown that the unique features of this new *Cornus* plant are stable and reproduced true to type in successive generations.

SUMMARY OF THE INVENTION

Plants of the new *Cornus* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Neil Z'. These characteristics in combination distinguish 'Neil Z' as a new and distinct *Cornus* plant:

1. Upright and compact plant habit.
2. Moderately vigorous growth habit.
3. Thick, glossy, relatively small and rugose leaves.

Plants of the new *Cornus* differ primarily from plants of the parent selection in the following characteristics:

1. Plants of the new *Cornus* are more compact than plants of the parent selection.

2. Leaves of plants of the new *Cornus* are glossier than leaves of plants of the parent selection.
3. Leaves of plants of the new *Cornus* are thicker and more rugose than leaves of plants of the parent selection.

Plants of the new *Cornus* can also be compared to plants of *Cornus sanguinea* 'Compressa', not patented. In side-by-side comparisons, plants of the new *Cornus* differ primarily from plants of 'Compressa' in the following characteristics:

1. Plants of the new *Cornus* are faster growing than plants of 'Compressa'.
2. Plants of the new *Cornus* are more cold hardy than plants of 'Compressa'.

BRIEF DESCRIPTION OF THE PHOTOGRAPHS

The accompanying colored photographs illustrate the overall appearance of the new *Cornus* plant showing the colors as true as it is reasonably possible to obtain in colored reproductions of this type. Colors in the photographs may differ slightly from the color values cited in the detailed botanical description which accurately describe the colors of the new *Cornus* plant.

The photograph on the first sheet comprises a side perspective view of a typical plant of 'Neil Z' grown in a container.

The photograph on the second sheet is a close-up view of a typical lateral branch of 'Neil Z'.

DETAILED BOTANICAL DESCRIPTION

The aforementioned photographs and following observations, measurements and values describe plants grown in one-gallon containers in an outdoor nursery in Grand Haven, Mich. and under cultural practices typical of commercial production. During the production of the plants, day temperatures ranged from 8° C. to 23° C. and night temperatures ranged from 1° C. to 15° C. Plants were one year old when the photographs and description were taken. In the following description, color references are made to The Royal Horticultural Society Colour Chart, 2001 Edition, except where general terms of ordinary dictionary significance are used.

Botanical classification: *Cornus sericea* 'Neil Z'.

Parentage: Naturally-occurring branch mutation of an unnamed selection of *Cornus sericea* (also known as *Cornus stolonifera*), not patented.

Rooting description:

*Type of cutting*.—Softwood cuttings.

*Time to initiate roots, summer*.—About 25 days at 20° C.

*Time to produce a rooted young plant, summer*.—About three months at 20° C.

*Root description*.—Thick; white in color.

*Rooting habit*.—Freely branching.

Plant description:

*Plant form and growth habit*.—Upright and compact deciduous shrub; slightly outwardly spreading; freely branching habit with about 23 lateral branches developing per plant; pinching enhances lateral branch development; moderately vigorous growth habit.

*Plant height*.—About 125 cm.

*Plant width* (*spread*).—About 75 cm.

*Lateral branches*.—Length: About 20 cm. Diameter: About 3 mm. Internode length: About 2.5 cm. Strength: Strong. Aspect: Erect to about 30° from vertical. Texture, new growth: Pubescent. Texture, mature stems: Smooth, glabrous. Color, developing stems, summer: Close to 144A. Color, developing stems, winter: Close to 59A. Color, fully developed stems: Close to 201A.

Foliage description:

*Arrangement*.—Opposite, simple.

*Length*.—About 1.8 cm.

*Width*.—About 1 cm.

*Shape*.—Narrowly elliptic to ovate.

*Apex*.—Acute.

*Base*.—Obtuse.

*Margin*.—Entire; undulate.

*Texture, upper and lower surfaces*.—Rugose; mostly glabrous; upper surface of developing leaves, pubescent.

*Luster, upper surface*.—Glossy.

*Luster, lower surface*.—Matte.

*Venation pattern*.—Pinnate.

*Color, summer*.—Developing leaves, upper surface: Close to 142B. Developing leaves, lower surface: Close to 138C. Fully expanded leaves, upper surface: Close to 139A to 139B; venation, close to 139B. Fully expanded leaves, lower surface: Close to 138A; venation, close to 138A.

*Color, autumn*.—Fully expanded leaves, upper surface: Close to 139B; venation, close to 139B. Fully expanded leaves, lower surface: Close to 138B; venation, close to 138B.

*Petiole*.—Length: About 4 mm. Diameter: About 1.5 mm. Texture, upper and lower surfaces: Smooth, glabrous. Color, upper and lower surfaces: Close to 138B.

Flower description: Flower initiation and development has not been observed on plants of the new *Cornus*.

Disease & pest resistance: Plants of the new *Cornus* have not been noted to be resistant to pathogens and pests common to *Cornus*.

Temperature tolerance: Plants of the new *Cornus* have been observed to tolerate high temperatures of about 35° C. and to be hardy to USDA Hardiness Zone 3.

It is claimed:

1. A new and distinct *Cornus* plant named 'Neil Z' as illustrated and described.

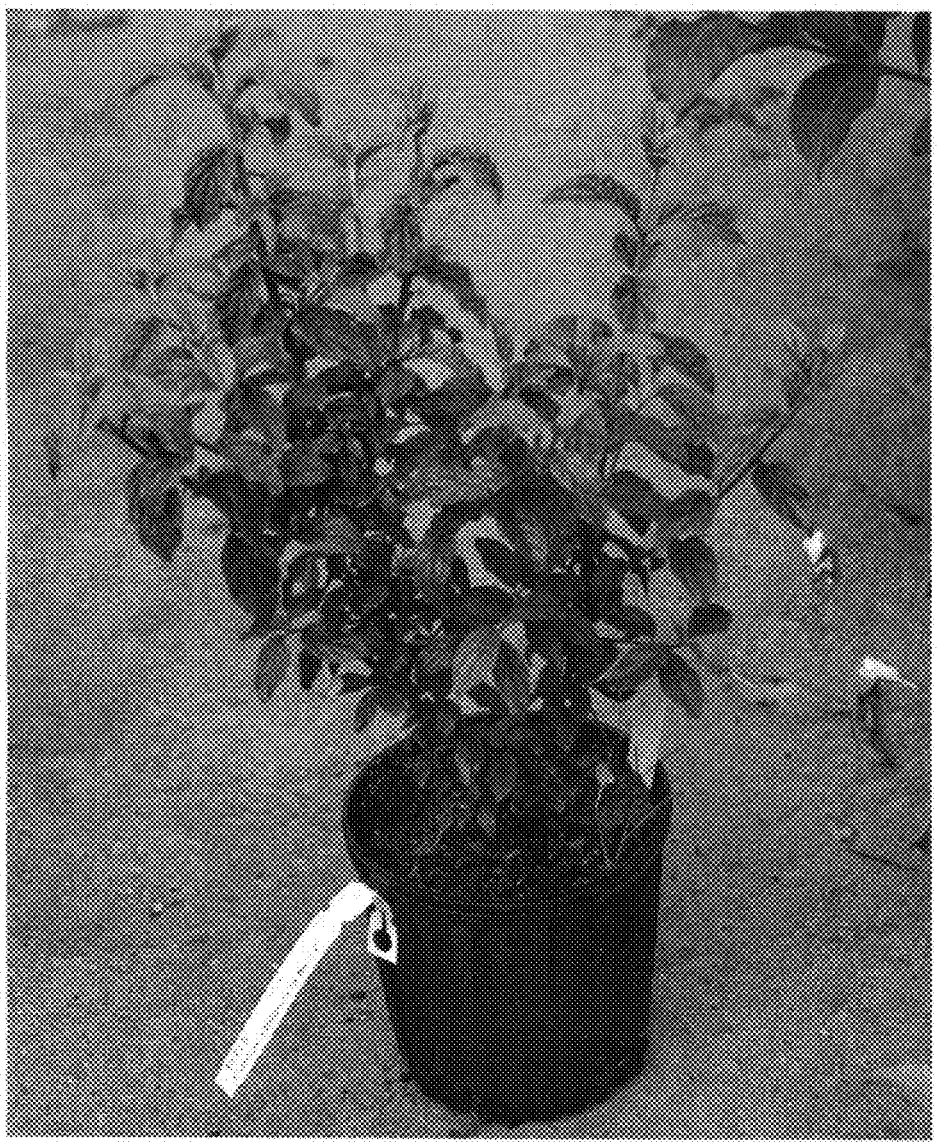

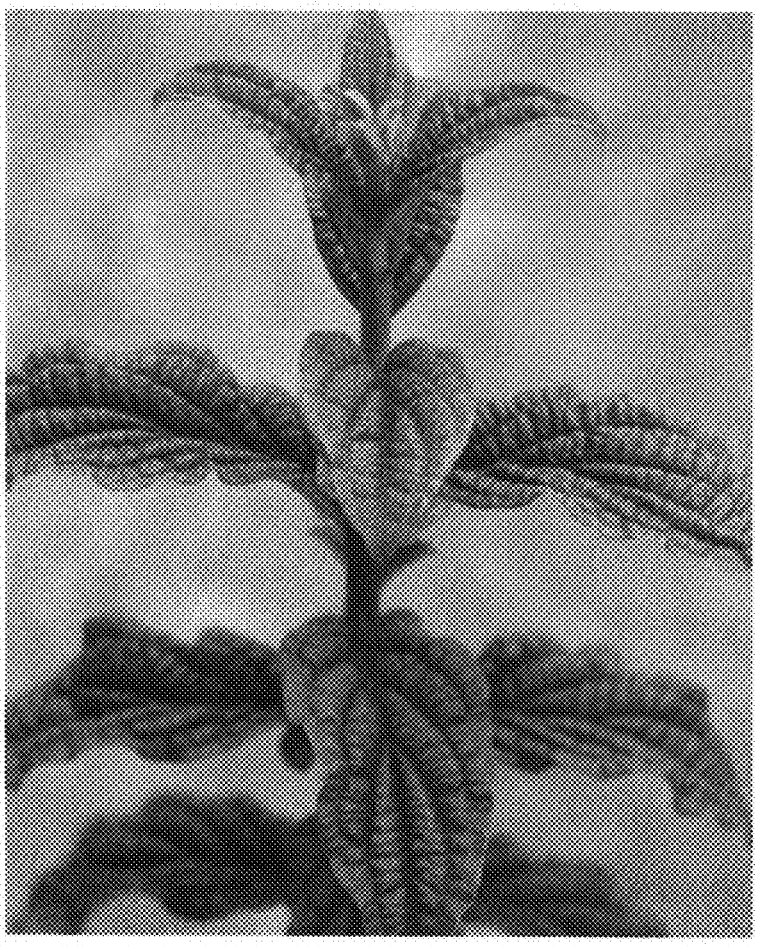

* * * * *